(12) United States Patent
Szelenyi et al.

(10) Patent No.: US 7,521,438 B1
(45) Date of Patent: Apr. 21, 2009

(54) COMBINATION OF LOTEPREDNOL AND $\beta_2$-ADRENOCEPTOR AGONISTS

(75) Inventors: Istvan Szelenyi, Schwaig (DE); Hildegard Kuss, Dresden (DE); Sabine Heer, Radebeul (DE); Juergen Engel, Alzenau (DE)

(73) Assignee: MEDA Pharma GmbH & Co. KG, Bad Homburg (DE)

( * ) Notice: Subject to any disclaimer, the term of this patent is extended or adjusted under 35 U.S.C. 154(b) by 144 days.

(21) Appl. No.: 10/089,449

(22) PCT Filed: Sep. 26, 2000

(86) PCT No.: PCT/EP00/09392

§ 371 (c)(1), (2), (4) Date: Jun. 28, 2002

(87) PCT Pub. No.: WO01/22956

PCT Pub. Date: Apr. 5, 2001

(30) Foreign Application Priority Data

Sep. 30, 1999 (DE) .................................. 199 47 235

(51) Int. Cl.
*A61K 31/56* (2006.01)

(52) U.S. Cl. .................... 514/177; 514/178; 514/169; 514/826

(58) Field of Classification Search .............. 514/177, 514/178, 167, 169
See application file for complete search history.

(56) References Cited

U.S. PATENT DOCUMENTS

| | | | |
|---|---|---|---|
| 4,710,495 A | 12/1987 | Bodor | |
| 4,996,335 A | 2/1991 | Bodor | |
| 5,830,490 A | 11/1998 | Weinstein et al. | |
| 6,461,591 B1 * | 10/2002 | Keller et al. | .................. 424/45 |

FOREIGN PATENT DOCUMENTS

| | | | |
|---|---|---|---|
| GB | 0 416 950 | * | 3/1991 |
| WO | WO 9831343 | * | 7/1998 |
| WO | WO 00/28979 | | 5/2000 |

OTHER PUBLICATIONS

Hardman et al. "Goodman & Gilman's The Pharmacological Basis of Therapeutics" (9th ed, 1996) p. 51 and 57-58.*
S. Nobel, et al., "Loteprednol Etabonate, Clinical Potential in the Management of Ocular Inflammation", Adis Drug Evaluation, Oct. 1998, pp. 329-339.
M. Palmqvist, et al., "Late asthmatic reaction decreased after pretreatment with salbutamol and formoterol, a new long-acting beta 2-agonist", Medline (R), 1992.
S.P. Clissold, et al., "Budesonide. A preliminary review of its pharmacodynamic properties and therapeutic efficacy in asthma and rhinitis", Medina (R), 1984.
R.J. Shaw, "Pharmacology of fluticasone propionate", Medline (R), 1994.
P.J. Barnes, et al., "Efficacy and safety of inhaled corticosteroids. New developments", Medline (R), 1998, Part A.
L. Bjermer et al., *Respiratory medicine*, vol. 91, No. 10 (1997), pp. 587-591.
T. van der Molen, *Thorax*, vol. 52, No. 6 (1997), pp. 535-539.

* cited by examiner

*Primary Examiner*—Sreeni Padmanabhan
*Assistant Examiner*—Shobha Kantamneni
(74) *Attorney, Agent, or Firm*—Crowell & Moring LLP

(57) ABSTRACT

The invention relates to a novel combination of a soft steroid, in particular loteprednol, and at least one $\beta_2$ adrenoceptor agonist for the simultaneous, sequential or separate treatment of allergies and/or airway disorders, medicaments comprising the combination, processes for the production of such medicaments and the use of the novel combination for the production of medicaments for the simultaneous, sequential or separate treatment of allergies and/or airway disorders.

6 Claims, No Drawings

COMBINATION OF LOTEPREDNOL AND $\beta_2$-ADRENOCEPTOR AGONISTS

The invention relates to a novel combination of a soft steroid, in particular loteprednol, and at least one $\beta_2$ adrenoceptor agonist for the simultaneous, sequential or separate treatment of allergies and/or airway disorders, medicaments comprising the combination, processes for the production of such medicaments and the use of the novel combination for the production of medicaments for the simultaneous, sequential or separate treatment of allergies and/or airway disorders.

BACKGROUND OF THE INVENTION

The number of patients who suffer from allergies and/or airway disorders, such as bronchial asthma, is increasing greatly worldwide.

Studies have shown that in the industrialized countries, 5-10% of the population suffer from asthma. Despite intensive research activity, the pathogenesis of bronchial asthma is still not completely clarified. Although in the past years numerous novel effective medicaments have been introduced into therapy, the treatment of this disorder is still not satisfactory. The fact that many asthmatics are not adequately treated is particularly alarming.

Bronchial asthma is a disorder of the lower airways. It is manifested in the contraction of the bronchial smooth musculature, which leads to acute dyspnea. In addition to this bronchoconstriction, however, chronic inflammation is prominent in the asthmatic process. Under certain circumstances, this chronic, always progressive inflammation can lead to further damage to the bronchial mucous membrane and thus to structural changes in the bronchial tree. As a result of this damage, irreversible constriction of the bronchi can occur. Accordingly, it is necessary to treat the asthmatics so that they are free from the acute asthmatic attacks and at the same time the inflammation underlying the disorder is reduced.

In order to remedy an acute asthma attack or to prevent its occurrence, $\beta_2$ mimetics are most suitable. $\beta_2$ agonists having short- and long-term action are now on the market. In order to avoid $\beta_2$ adrenoceptor-related side effects, which under certain circumstances can be life-threatening, the long-acting $\beta_2$ mimetics should only be administered twice in the course of the day. However, use can be made, if required, of the so-called short-term $\beta_2$ mimetics. Asthmatics like to employ $\beta_2$ mimetics, because they immediately eliminate the acute symptoms. The antiinflammatory medicaments, such as corticosteroids, are used less deliberately, as they do not eliminate the apnea, and thus the patient is conscious of no immediate improvement in his condition.

Loteprednol belongs to the so-called soft corticosteroids. These so-called soft corticosteroids (soft steroids) are distinguished in that they are inactivated by a so-called one-step reaction, i.e. by hydrolases, esterases without involvement of the mainly hepatically located cytochrome P450 monooxidase enzymes. Owing to this, only very low plasma concentrations occur, if at all, which are not sufficient to produce the classical corticosteroid side effects such as retardation of growth, osteoporosis or increase in the intraocular pressure.

Surprisingly, it has now been found that the novel combination of a soft steroid and at least one $\beta_2$ adrenoceptor agonist is advantageous in the treatment of allergies and/or airway disorders in mammals, in particular in man. The administration of the combination for topical treatment by inhalation can be carried out simultaneously, sequentially or separately.

According to one embodiment of the invention loteprednol and its pharmaceutically acceptable esters, in particular loteprednol etabonate, is a particularly suitable soft steroid. The preparation of loteprednol and loteprednol etabonate is described, for example, in German Patent No. DE 31 26 732, the corresponding U.S. Pat. No. 4,996,335 and the corresponding Japanese Patent No. JP-89 011 037.

Further suitable soft steroids according to the invention are described, for example, in German Patent No. 37 86 174, the corresponding European Patent No. EP 0 334 853 and the corresponding U.S. Pat. No. 4,710,495.

Loteprednol is licensed for the treatment of allergic conjunctivitis and uveitis in the United States. In this case, it was shown that topically administered loteprednol does not increase the intraocular pressure in contrast to the non soft corticosteroids and could not be detected in the plasma (Noble and Goa, BioDrugs 10:329-339, 1998). As a result of the one-step reaction mentioned, in the case of administration by inhalation, the swallowed portion is also immediately inactivated in the liver. This portion, too, can therefore produce no side effects.

$\beta_2$ mimetics ($\beta_2$ sympathomimetics) are medicaments which selectively stimulate the $\beta_2$ adrenoreceptors and thereby relax the bronchi. Moreover, via the inhibition of the release of some endogenous mediators, they also inhibit edema formation and promote mucociliary clearance. They remedy the acute attack (apnea as a result of bronchoconstriction) very rapidly. Their action lasts for different lengths of time: that, for example, of salbutamol (short-term $\beta_2$ mimetics) for 4-6 hours; that of formoterol or salmeterol (long-term $\beta_2$ mimetics) for up to 12 hours. A great advantage of formoterol compared to salmeterol is that the bronchodilatory action of formoterol not only lasts long-term but occurs immediately as in the case of the short-term $\beta_2$ mimetics (Palmqvist et al., J. Allergy Clin. Immunol. 89:844-849, 1992).

Formoterol, salmeterol and salbutamol can also be used in the form of the pharmaceutically tolerable salts, formoterol fumarate, salmeterol xinafoate and salbutamol sulfate being preferred. Formoterol fumarate dihydrate is particularly preferred.

According to a particular embodiment, reproterol or its pharmaceutically tolerable salts can be used as a $\beta_2$ mimetic, reproterol hydrochloride being preferred.

These active compounds are administered as an inhalation with the aid of metered aerosols (MDI) or powder inhalers (MPDI). As a result of the inhalative administration, not only the dose but also the occurrence of possible undesired effects can be reduced.

The present invention describes the combination of a soft corticosteroid, preferably loteprednol and a $\beta_2$ mimetic, preferably salbutamol or formoterol, it being possible to administer the individual component of this combination by inhalation in the therapy of bronchial asthma simultaneously, one after the other or individually. A fixed combination of the two active components is particularly advantageous, as in this case the patient only needs a metered aerosol and thus the effective treatment is easier for the patient.

The reasons for the combination described in the invention can be supported experimentally.

In vitro investigations were carried out for influencing the release of the proinflammatory cytokine TNFα in human blood diluted 1:5. Stimulation was carried out using lipopolysaccharide (LPS) of *Salmonella abortus* equi (10 μg/ml) over the course of 24 h at 37° C. and 5% $CO_2$ in an incubator. The TNFα release was carried out using an ELISA, composed from antibodies from Pharmigen. The results were indicated as the percentage inhibition of LPS-induced TNFα release (Table 1).

TABLE 1

Inhibition of the TNFα release in human blood diluted 1:5 (n = 8)

| Active compound | Concentration in [μmol/l] | Inhibition of TNFα release |
|---|---|---|
| Salbutamol | 10 | 17% |
| Loteprednol | 0.001 | 1% |
| Loteprednol + salbutamol | 0.001 + 10 | 44*% |

*(p < 0.01)

In vivo investigations were carried out on guinea pigs which had been actively sensitized on two successive days by double intraperitoneal (i.p.) injection of a suspension of ovalbumin and aluminum hydroxide in physiological saline solution. Two weeks after the sensitization, they were exposed short-term to an aerosol of ovalbumin solution in an atomization box. As a result of the inhalatory allergen provocation, 24 hours later a great increase in the number of eosinophilic granulocytes (inflammatory cells) in the lung occurs. Similarly to the asthmatics, at this time (24 hours after the allergic provocation) lavage of the lung takes place. The number of eosinophilic granulocytes in the pulmonary lavage fluid is determined using a hemacytometer (Technicon H1E). The percentage inhibition of the eosinophilic granulocytes by test substances is then calculated.

In order to be able to give the active compounds in exactly metered form intrapulmonarily, they are administered to the animals directly into the lungs as a powder (mixed with lactose) by means of a catheter tied into the trachea. The administration of the active compounds is carried out before the allergen provocation under brief ketamine/xylazine anesthesia, from which the animals immediately awake. The results are compiled in Table 2.

TABLE 2

The action of loteprednol and formoterol alone and in combination on late-phase eosinophilia in actively sensitized guinea pigs

| Active compound | Dose in mg/kg intrapulmonarily | Inhibition of eosinophilia | Number of animals |
|---|---|---|---|
| Loteprednol | 0.001 | 10.5% | 5 |
|  | 0.003 | 21.8% | 5 |
| Formoterol | 0.0001 | 4.1% | 4 |
|  | 0.001 | 20.4% | 4 |
| Loteprednol + formoterol | 0.001 + 0.0001 | 36.1%* | 6 |
|  | 0.003 + 0.0001 | 45.2%* | 6 |
|  | 0.001 + 0.001 | 64.5%** | 6 | significant against allergen provocation control:
*(0.05);
**(p < 0.01)

When the soft corticosteroid loteprednol was investigated in the dose 0.001 mg/kg or the $\beta_2$ agonist formoterol in the dosages 0.0001 mg/kg and 0.001 mg/kg on intrapulmonary powder administration, no inhibition or a marginal inhibition of the allergically induced late-phase eosinophilia occurred. When both active compounds were given simultaneously, the number of eosinophilic granulocytes in the pulmonary lavage fluid 24 hours after allergen provocation were (significantly) reduced by 39.1% and 64.5% respectively.

As already briefly mentioned, the corticosteroids cause numerous side effects which often restrict their clinical use. Particularly in the case of children, corticosteroids influence growth. In general, it is possible to say that the growth of the asthmatic children treated with corticosteroids remains behind that of those not treated with corticosteroids by one centimeter (1 cm) annually. This undesired side effect applies to all corticosteroids on the market at the present time such as, for example, budesonide or fluticasone (cf. Clissold S. P. and R. C. Heel., Drugs 28:485-518, 1984; Shaw R. J., Respiratory Medicine 88(Suppl.A): 5-8, 1994; Barnes P. J. et al., Am. J. Resp. Critical Care Med. 157(3) Suppl. Part 2: p 1-p 53, 1998;). In the case of a corticosteroid, it could be a great advantage if this corticosteroid did not influence the development of growth in children. In order to determine the potential for side effects in animal experiments, the influence of the corticosteroids on the thymus gland of the rat was investigated.

In the first experiment, loteprednol was administered subcutaneously 1× daily over the course of 5 days to grown rats in comparison to fluticasone, beclomethasone and budesonide. Up to a dose of 10 mg/kg s.c. of loteprednol, no significant reduction in the thymus weight compared with control animals was measured. Fluticasone (1 mg/kg s.c.), beclomethasone (1 mg/kg s.c.) and budesonide (2 mg/kg s.c.) showed a significant reduction in the thymus weights (see Table 3).

TABLE 3

Action of corticosteroids in high doses on the thymus weight of rats on repeated subcutaneous application (5 days; 1 × each daily)

| Active compound | Dose in mg/kg subcutaneous dose multiple dose (5 days, 1 × each daily) | % reduction in the thymus weight (mg/100 g BW) compared with lactose control 0 |
|---|---|---|
| Loteprednol | 1 | 15 |
|  | 10 | 28 |
| Fluticasone | 1 | 65 (p < 0.01) |
| Beclomethasone | 1 | 51 (p < 0.01) |
| Budesonide | 2 | 89 (p < 0.05) |

In the second experiment, the influence of loteprednol on the thymus development of young rats (21 days old at the start of the experiment) was intensively investigated in comparison to budesonide and fluticasone (see Table 4). After an intrapulmonary long-term administration of the active compound in powder form over the course of 29 days (1× daily) by means of a tube, at the end of the experiment the thymus glands were removed and the organ weight per 100 g of body mass was determined. Fluticasone in the dose 1.0 mg/kg and budesonide in the dose 0.5 mg/kg caused a significant reduction in the thymus weight compared with control animals which were treated with lactose. On intrapulmonary long-term administration, loteprednol exhibited a marked reduction of the thymus weight only in the high dose of 20 mg/kg.

The therapeutic breadth of the corticosteroids was determined with the aid of the quotient of the dose (mg/kg) with significant thymus involution (toxic dose) on repeated intrapulmonary administration over the course of 29 days (1× daily) and the therapeutic dose. The therapeutic dose was determined in the asthma model of late-phase eosinophilia on actively sensitized brown Norway rats. The active compound was administered to the sensitized brown Norway rats under anesthesia intrapulmonarily 2 hours before an allergen provocation (challenge) and 24 hours later the lungs of the animals were lavaged under deep anesthesia. The number of eosinophilic granulocytes in the pulmonary lavage fluid of untreated and active compound-treated rats was then determined. Corticosteroids such as loteprednol inhibit the infiltration of eosinophils into the lung after allergen provocation. From the inhibitory values of increasing active compound doses, the 50% inhibitory dose ($ID_{50}$ in µg/kg) on the allergically induced late-phase eosinophilia was determined.

For loteprednol, a great therapeutic breadth having a quotient of $45.5 \times 10^3$ was determined. Budesonide ($5 \times 10^3$) and fluticasone ($33 \times 10^3$) showed markedly smaller quotients (see Table 4).

TABLE 4

Therapeutic breadth of corticosteroids in rats on intrapulmonary powder application: Quotient of toxic dose (mg/kg) with significant thymus involution on repeated administration (29 days) and therapeutic dose ($ID_{50}$ µg/kg) on single administration in late-phase eosinophilia in actively sensitized brown Norway rats.

| Active compound | Therapeutic dose in late-phase eosinophilia $ID_{50}$ in µg/kg | Toxic dose with significant thymus involution in mg/kg | Quotient of toxic dose: therapeutic dose |
|---|---|---|---|
| Dosage | Single administration, 2 h before allergen provocation | Repeated administration, 29 days, 1 × daily | $\times 10^3$ |
| Application | Intrapulmonary | Intrapulmonary | |
| Loteprednol | 0.44 | 20 | 45.5 |
| Fluticasone | 0.03 | 1 | 33 |
| Budesonide | 0.1 | 0.5 | 5 |

Thus loteprednol is clearly superior to the steroids fluticasone and budesonide with respect to the therapeutic breadth.

The amount of soft steroid and $\beta_2$ adrenoreceptor agonist to be administered depends, inter alia, on the efficacy, duration of action and the type and the severity of the disease to be treated. The constitution and the age of the patient are furthermore of importance. The ratio formoterol to loteprednol can be, for example, in the range between 2:1 and 1:500, preferably between 1:8 and 1:63, particularly preferably between 1:8 and 1:42, in each case based on the weight. Thus a ratio of 1:10 to 1:35, for example, has proven favorable. The two components can be administered simultaneously, sequentially or separately.

Because of the long duration of action of both active compounds, dosage twice daily is preferred. An appropriate dose range of formoterol is between 6 and 100 µg/day, a dose range of 6 to 48 µg/day being preferred. For loteprednol, the daily appropriate dose range can be specified as 50-2000µ/day. A daily dosage of 100 to 1000 µg/day is preferred. Because of the harmlessness detected in the animal experiment and also in the treatment of allergic conjunctivitis, loteprednol in the combination can also be given at a daily dose of up to 3000 µg.

The combination according to the invention of soft steroid and $\beta_2$ adrenoreceptor agonist can be used in the treatment of airway disorders, such as disorders of the lower airways, chronic obstructive airway disorders (COPD), e.g. bronchial asthma, chronic obstructive bronchitis, pulmonary emphysema with reversible obstruction, bronchial asthma and other bronchial disorders. It can also be used for the treatment of allergies.

EXAMPLE 1

Metered Aerosol with 6 µg of Formoterol Fumarate Dihydrate and 200 µg of Loteprednol Etabonate Per Stroke 1000 g of 2H-heptafluoropropane (=propellant 227) are cooled to a temperature of approximately −55° C. and mixed with stirring with a solution of 11.7 g of polyoxyethylene 25-glyceryl trioleate (commercial name: Tagat® TO, Goldschmidt AG) in 11.7 g of absolute ethanol. 3.34 g of micronized loteprednol etabonate and 0.1 g of micronized formoterol fumarate dihydrate are then added and the resulting suspension is intensively homogenized. The suspension is made up to 1170.0 g with cooled propellant 227 and with further stirring and cooling and then dispensed into metal cans which are closed with metering valves which release 50 µl of the suspension per stroke.

6 µg of formoterol fumarate dihydrate and 200 µg of loteprednol etabonate are released per stroke.

EXAMPLES 2 TO 4

The procedure is as in Example 1, but instead of the amounts of active substance mentioned there the following amounts are employed:

| | Active compound employed per batch | | Active compound released per stroke | |
|---|---|---|---|---|
| Example | Formoterol fumarate dihydrate | Loteprednol etabonate | Formoterol fumarate dihydrate | Loteprednol etabonate |
| 2 | 0.2 g | 3.34 g | 12 µg | 200 µg |
| 3 | 0.2 g | 8.35 g | 12 µg | 500 µg |
| 4 | 0.4 g | 8.35 g | 24 µg | 500 µg |

EXAMPLE 5

Powder Inhalation with 6 µg of Formoterol Fumarate Dihydrate and 200 µg of Loteprednol Etabonate Per Individual Dose 0.51 g of micronized formoterol fumarate dihydrate is mixed with 10 g of α-lactose monohydrate, and the mixture is sieved through a sieve of mesh width 0.3 mm and mixed in a Turbula mixer (manufacturer: Bachofen, Basle, Switzerland) for 10 minutes.

17 g of loteprednol etabonate are mixed with 340 g of α-lactose monohydrate, the mixture is sieved through a sieve of mesh width 0.3 mm and mixed in a Turbula mixer for 10 minutes.

The two mixtures are combined, and the mixture is again sieved through a sieve of mesh width 0.3 mm, made up to 1020 g with α-lactose monohydrate and again mixed for 30 minutes in the Turbula mixer.

The mixture is filled into a powder inhaler which releases 12 mg of the mixture per individual dose. 12 mg of the mixture contain 6 µg of formoterol fumarate dihydrate and 200 µg of loteprednol etabonate.

EXAMPLES 6 TO 8

The procedure is as in Example 5, but the following amounts are employed instead of the amounts of active substances mentioned there:

| Example | Active compound employed per batch | | Active compound released per stroke | |
|---|---|---|---|---|
| | Formoterol fumarate dihydrate | Loteprednol etabonate | Formoterol fumarate dihydrate | Loteprednol etabonate |
| 6 | 1.02 g | 17.0 g | 12 µg | 200 µg |
| 7 | 1.02 g | 42.5 g | 12 µg | 500 µg |
| 8 | 2.04 g | 42.5 g | 24 µg | 500 µg |

The invention claimed is:

1. A powdered pharmaceutical composition consisting essentially of
   an efficacious amount of (i) loteprednol or loteprednol etabonate; and (ii) at least one $\beta_2$ adrenoreceptor agonist selected from the group consisting of salbutamol, reproterol, salmeterol, formoterol, and pharmaceutically tolerable salts there of,
   for administration by inhalation, wherein the pharmaceutical composition is formulated in a powdered form.

2. The powdered pharmaceutical composition according to claim 1, consisting essentially of
   (i) loteprednol or loteprednol etabonate; and
   (ii) formoterol.

3. The powdered pharmaceutical composition according to claim 1, consisting essentially of
   (i) loteprednol or loteprednol etabonate, and
   (ii) salmeterol.

4. The powdered pharmaceutical composition according to claim 1, consisting essentially of
   (i) loteprednol or loteprednol etabonate; and
   (ii) reproterol.

5. A method for the treatment of asthma bronchiale in a patient, the method comprising:
   administering to the patient an efficacious amount of (i) loteprednol or loteprednol etabonate and (ii) at least one $\beta_2$ adrenoceptor agonist selected from the group consisting of salbutamol, reproterol, salmeterol, formoterol, and pharmaceutically tolerable salts there of,
   wherein a pharmaceutically acceptable excipient or a vehicle is added.

6. A process for the preparation of a pharmaceutical composition for the treatment of asthma bronchiale, the process comprising:
   combining (i) an effective amount of the active compound loteprednol or loteprednol etabonate and (ii) an effective amount of at least one $\beta_2$ adrenoceptor agonist selected from the group consisting of salbutamol, reproterol, salmeterol, formoterol, and pharmaceutically tolerable salts there of,
   wherein the loteprednol or loteprednol etabonate and one or more $\beta_2$ adrenoceptor agonists are mixed individually or together,
   wherein a pharmaceutically acceptable excipient or a vehicle is added, and
   wherein the composition thus obtained is converted into a powdered form suitable for inhalations.

* * * * *